(12) United States Patent
Shacham

(10) Patent No.: US 9,375,168 B2
(45) Date of Patent: Jun. 28, 2016

(54) APPARATUS AND METHOD FOR COLLECTING CORD BLOOD

(75) Inventor: Miki Shacham, Tel Aviv (IL)

(73) Assignee: SITUGEN LTD., Tel Aviv (IL)

( * ) Notice: Subject to any disclaimer, the term of this patent is extended or adjusted under 35 U.S.C. 154(b) by 173 days.

(21) Appl. No.: 12/066,698

(22) PCT Filed: Sep. 11, 2006

(86) PCT No.: PCT/IL2006/001064
§ 371 (c)(1),
(2), (4) Date: Mar. 13, 2008

(87) PCT Pub. No.: WO2007/031999
PCT Pub. Date: Mar. 22, 2007

(65) Prior Publication Data
US 2008/0228153 A1 Sep. 18, 2008

(30) Foreign Application Priority Data
Sep. 15, 2005 (IL) .......................................... 170881

(51) Int. Cl.
*A61B 19/00* (2006.01)
*A61B 5/15* (2006.01)

(52) U.S. Cl.
CPC ..................... *A61B 5/1405* (2013.01)

(58) Field of Classification Search
USPC .......... 604/356, 317, 321–323, 326; 600/573; 606/119, 120
See application file for complete search history.

(56) References Cited

U.S. PATENT DOCUMENTS

| 5,053,025 A | 10/1991 | Knippscheer |
| 5,372,581 A | 12/1994 | Anderson |
| 5,575,796 A | 11/1996 | King et al. |
| 5,817,103 A * | 10/1998 | Bell .............................. 606/120 |
| 5,915,384 A * | 6/1999 | Grossman et al. ............ 600/573 |
| 6,190,368 B1 | 2/2001 | Kuypers et al. |
| 6,302,854 B1 | 10/2001 | Paderni |
| 2002/0183679 A1 | 12/2002 | Deverre |
| 2005/0010189 A1* | 1/2005 | Toomey et al. ............... 604/403 |
| 2007/0112280 A1 | 5/2007 | Richard |

FOREIGN PATENT DOCUMENTS

FR 2861282 4/2005

OTHER PUBLICATIONS

Intl Search Report of PCT/IL06/001064, Apr. 4, 2007.
Intl Prelim Rep Patentabi of PCT/IL06/001064, Dec. 14, 2007.

* cited by examiner

*Primary Examiner* — Tatyana Zalukaeva
*Assistant Examiner* — Ginger T Chapman
(74) *Attorney, Agent, or Firm* — Naomi Assia Law Offices

(57) ABSTRACT

The invention is devices and methods for collecting fetal blood from the umbilical cord and placenta after the birth of a baby. Embodiments of the invention are open circuit devices and methods that allow collection of relatively large quantities of cord blood while reducing the risk of contamination to levels lower than those presently associated with closed circuit systems. Other embodiments are methods and devices for use in closed system procedures that increase the amount of blood collected and also reduce the amount of contamination in presently employed closed systems.

11 Claims, 8 Drawing Sheets

APPARATUS AND METHOD FOR COLLECTING CORD BLOOD

FIELD OF THE INVENTION

This invention relates to the collection of cord blood. More specifically, this invention describes an apparatus and a method for collecting human fetal blood from the placenta and the umbilical cord, following the birth of a baby.

BACKGROUND OF THE INVENTION

In recent years there has been a growing interest in the collection of human fetal blood. Such blood is a source of numerous blood factors that have important commercial and therapeutic uses in a number of different fields, such as tissue culture, bone marrow transplantation, stem cell collection, pharmacology, and biological research. Currently, the sole commercial source of human fetal blood is blood obtained from the placenta and umbilical cord of newborns after delivery. This blood is often referred to as cord blood, as it is typically obtained by draining the placenta and umbilical cord through the severed umbilical cord after delivery.

The most commonly used commercial method for collecting cord blood is venipuncture, which is known in the art as a closed circuit system. Typically, cord blood is collected through one needle inserted in the vein of the umbilical cord, into a bag, though in some procedures, a syringe may replace the bag. In contrast, an open circuit procedure is one where blood flows freely from the severed end of the umbilical cord into a container. Closed-circuit methods aim mostly at reducing the risk of contamination of the collected blood, which occurs very commonly during the open-circuit procedures. However, the main advantage of open-circuit systems is that there is no resistance to the flow of blood, and therefore, the average amount of blood collected by open circuit systems is larger than the average amount collected when using closed-circuit methods. Consequently, an open-circuit method, in which the blood sample was kept sterile, thereby avoiding contamination, would be very beneficial in the art.

In order to collect as much blood as possible, the force of gravity is exploited, hence, the placenta is held at a higher position than the collecting implement. In addition, the placenta is usually "milked", either by the contractions of the uterus, if still in the mother's body, or, if not, it may be compressed by some sort of apparatus, such as a container connected to an inflatable bladder. Some procedures for collecting cord blood compress the umbilical cord as well as the placenta.

Many methods for collecting cord blood have been developed. Several such methods and devices relating to various types of systems for collecting blood from the umbilical cord are disclosed in, for example, the following patents: U.S. Pat. Nos. 5,372,581, 5,575,796 and 5,053,025.

Paderni discloses in U.S. Pat. No. 6,302,854 a general method for collecting fluids, particularly cord blood. According to Paderni's method, a portion of the cord is cleaned, disinfected, and cut and then the cord is coupled to the connection system, which locks the cord in place. No description of how these steps are accomplished is provided in the patent. Finally, the connection system is then connected to a collection container. After expulsion from the mother's body, the placenta is placed in a container where positive pressure is applied to it. Optionally, Paderni states, without describing how, that negative pressure can be applied to the blood collection container in order to facilitate the outflow of blood from the umbilical cord.

In U.S. Pat. No. 6,190,368, to Kuypers, et. al., is described an apparatus and a method for collecting blood from an umbilical cord. The apparatus disclosed consists mainly of a housing having an inner region adapted to retain an umbilical cord in a desired location and an opening through which the cord extends from this inner region to a region external to the housing. In their procedure, the cord is cut by a blade coupled to the housing and through the newly cut end of the umbilical cord the blood flows, aided by gravity, into a blood collection region of the housing. In addition they disclose a receiving container for the placenta which is equipped with an inflatable bladder or other means for compressing the placenta.

Many other methods and apparatuses for collecting cord blood are disclosed in the prior art. Some of these methods describe "open-circuit" systems, in which the collected blood is vulnerable to contamination. In addition, many of the devices are expensive, and sometimes complicated to use, requiring a great deal of skill on part of the person collecting the blood.

The main limitation of the prior art is the amount of uncontaminated cord blood collected. This amount is highly important since it determines the quantity of stem cells that can be extracted from the collected sample. Currently, the average amount of blood collected is 80 ml, though a skilled collector might collect up to 150 ml of the approximately 250 ml present. The amount of stem cells extracted form an average blood sample is usually sufficient for transplants in subjects weighing up to about 44 kg, therefore not allowing a treatment solution conditions arising after childhood. The amount of blood collected is usually very dependent on the skill of the collector.

After birth there is a fast deterioration in the blood vessel structure and coagulation of the blood takes place very rapidly. Since most existing collection procedures are comparatively slow, much of the cord blood coagulates in the placenta and in the umbilical cord and many blood vessels collapse, causing blood to be essentially trapped in the placenta and the umbilical cord before it can be collected.

It is highly desirable to develop a procedure which will maximize the amount of uncontaminated blood extracted from the placenta and the umbilical cord. Such a procedure would be fast, being completed before coagulation and collapse of vessels reduces the amount of blood collected, and employ a semi-automatic collection device that would not require any special skill on part of the collector to use. In addition, contamination must be prevented, and the collection kit should be disposable and inexpensive.

It is an object of this invention to provide an apparatus, which comprises a hermetically closed and disinfected device for collecting cord blood.

It is another object of this invention to provide a method of using said apparatus for collecting cord blood, which will overcome the drawbacks of the prior art mainly by increasing the amount of uncontaminated blood collected so that the number of stem cells extracted will be sufficient for transplanting in a grown person.

It is another object of this invention to provide an improved apparatus and method for a closed-circuit collection of cord blood.

It is another object of this invention to provide an apparatus which even an inexperienced person can use efficiently.

It is a further object of this invention to provide a comparatively fast method of collecting cord blood.

It is another purpose of this invention is to provide an inexpensive, disposable collection kit.

Other purposes and advantages of this invention will appear as the description proceeds.

SUMMARY

In a first aspect the invention is a collection apparatus for collecting fetal blood from the umbilical cord and placenta after the birth of a baby. The apparatus comprises components that allow an open circuit collection procedure to be carried out in a hermetically closed sterile environment, thereby preventing contamination of the fetal blood by contact with the environment surrounding the collection apparatus during the entire blood collection process.

A preferred embodiment of the collection apparatus of the invention comprises:

a. A holder device that can be opened and closed to receive and hold the upper part of the severed end of the umbilical cord. The holder device comprises elements that allow it to be reversibly attached to the disinfection compartment.
b. A disinfection compartment that receives the lower part of the severed end of the umbilical cord. The disinfection compartment comprises elements that allow it to be reversibly attached to the holder device, a connection to the outside through which material can be introduced to disinfect its interior, and a nipple fitted with a filter and valve through which clean air can enter or exit the interior of the disinfection chamber. and
c. At least one blood collection vessel connected to and in hermetic fluid communication with the interior of the disinfection compartment.

In some embodiments, the blood collection vessel is an integral part of the apparatus. The blood collection vessel may comprise a hub for connecting to one or more external blood collection objects. In other embodiments the blood collection vessel is not an integral part of the apparatus and comprises one or more syringes, blood collection bags or multi sample vacuum tube holders. The holder device preferably comprises an absorbent material on its interior.

In another aspect the invention is a method of using the apparatus to collect fetal blood from the umbilical cord and the placenta after the birth of a baby. The method of the invention comprises the steps:

a. clamping the umbilical cord using two cord clamps;
b. severing the umbilical cord between the two cord clamps;
c. opening the holder device;
d. inserting the severed end of the portion of the umbilical cord that is connected to the placenta into the holder device such that the cord clamp rests on the outer top surface of the holder device and part of the cord dangles below the bottom of the holder device;
e. closing the holder device;
f. placing the holder device on top of the disinfection compartment while inserting the dangling end of the cord into the disinfection compartment until the cord is straight and the tip of the cord is in side the disinfection compartment;
g. engaging the elements on the holder device with the elements on the disinfection compartment to attach them together;
h. opening the valve to allow free flow of clean air into or out of the interior of the disinfection compartment through the filter;
i. opening the clamp allowing a few drops of blood to flow out of the tip of the cord;
j. closing the clamp;
k. disinfecting the interior of the disinfection compartment and the end of the umbilical cord by injecting disinfectant into the disinfection compartment;
l. drawing out the blood and disinfectant;
m. optionally repeating steps (k) and (l) one or more times;
n. closing the valve; and
o. removing the cord clamp from the umbilical cord, thereby allowing the blood to flow freely into the collection vessel.

In another aspect the invention is a system for performing a closed circuit collection procedure of collecting fetal blood from the umbilical cord and the placenta after the birth of a baby. The system comprises:

a. a blood collection bag;
b. three or more needles ; and
c. tubing to connect the needles to the bag.

In a preferred embodiment of the system at least one of the needles has a larger diameter than of a 16 G needle. At least one of the needles may be an IV-cannula. Preferably the bag has a capacity that is large enough to collect at least 200 cc of cord blood. The bag may contain anticoagulant solution or powder.

In another aspect the invention is a method for using the close-circuit system of the invention to collect fetal blood from the umbilical cord and the placenta after the birth of a baby. The method comprises the steps:

a. clamping the umbilical cord using two cord clamps;
b. severing the umbilical cord between the two cord clamps;
c. inserting one of the needles into the vein near the clamped end of the portion of the cord that is attached to the placenta, thereby allowing the blood to flow into the collection bag;
d. inserting another needle into the vein at a location above the first needle when the flow of blood through the first needle slows down;
e. repeating step d one or more times until all of the needles have been inserted into the vein and blood ceases to flow into the bag; and
f. sealing the bag.

Each of the needles may be removed from the vein after a new needle has been inserted.

In another aspect the invention is a method for using the close-circuit system of the invention to collect fetal blood from the umbilical cord and the placenta after the birth of a baby using a close-circuit system. The method comprises the steps:

a. severing the umbilical cord between the two cord clamps;
b. inserting one of the needles into the vein in the cord;
c. inserting another one of the needles into one of the arteries in the cord;
d. inserting another one of the needles into the other artery in the cord;
e. allowing the blood from the vein and the arteries to flow into the blood collection bag; and
f. sealing the bag when blood ceases to flow into it.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

The invention is devices and methods for collecting fetal blood from the umbilical cord and placenta after the birth of a baby. Embodiments of the invention are open circuit devices and methods that allow collection of relatively large quantities of cord blood while reducing the risk of contamination to levels lower than those presently associated with closed circuit systems. Other embodiments are methods and devices for use in closed system procedures that increase the amount of blood collected and also reduce the amount of contamination in presently employed closed systems. It is to be understood that the following description of specific devices and methods is given for purposes of illustrating the general principles of the invention only. In particular specific dimensions and materials are specified for illustrative purposes only.

Generally, after child birth the umbilical cord is clamped using two cord clamps, a re-openable one on the mother's side and another on the baby's side. The cord is then cut between these two cord clamps, leaving a loose cord on the mother's side. After the birth of the child occurs what is known as the birth of the placenta, i.e. the expulsion of the placenta from the mother's body. Most of the conventional methods used in hospitals for collecting cord blood are optimally applied before the birth of the placenta, since the uterine contractions facilitate the outflow of blood from the placenta through the umbilical cord.

Embodiments of the invention are methods and apparatuses for carrying them out, which can be described as open-circuit procedures since the involve collection of the cord blood by allowing it to drain freely from the open, freshly cut end of the umbilical cord. The blood flows into a hermetically closed and disinfected collection chamber. The method therefore combines the major advantage of the open method, i.e. allowing the amount of cord blood collected to be sufficiently large that the number of stem cells in the sample will be sufficient for future implantation into an adult, with that of the closed-circuit one, i.e. the blood sample is not contaminated. In addition the apparatus is easy to use, allowing good results to be obtained by inexperienced personnel; inexpensive, preferably disposable; and the process of collecting blood is fast. The collection of blood can begin before or after the birth of the placenta, however it preferably begins before the birth of the placenta to reduce the amount of clotting and collapse of blood vessels, thereby maximizing the amount of blood collected.

Figure 1:
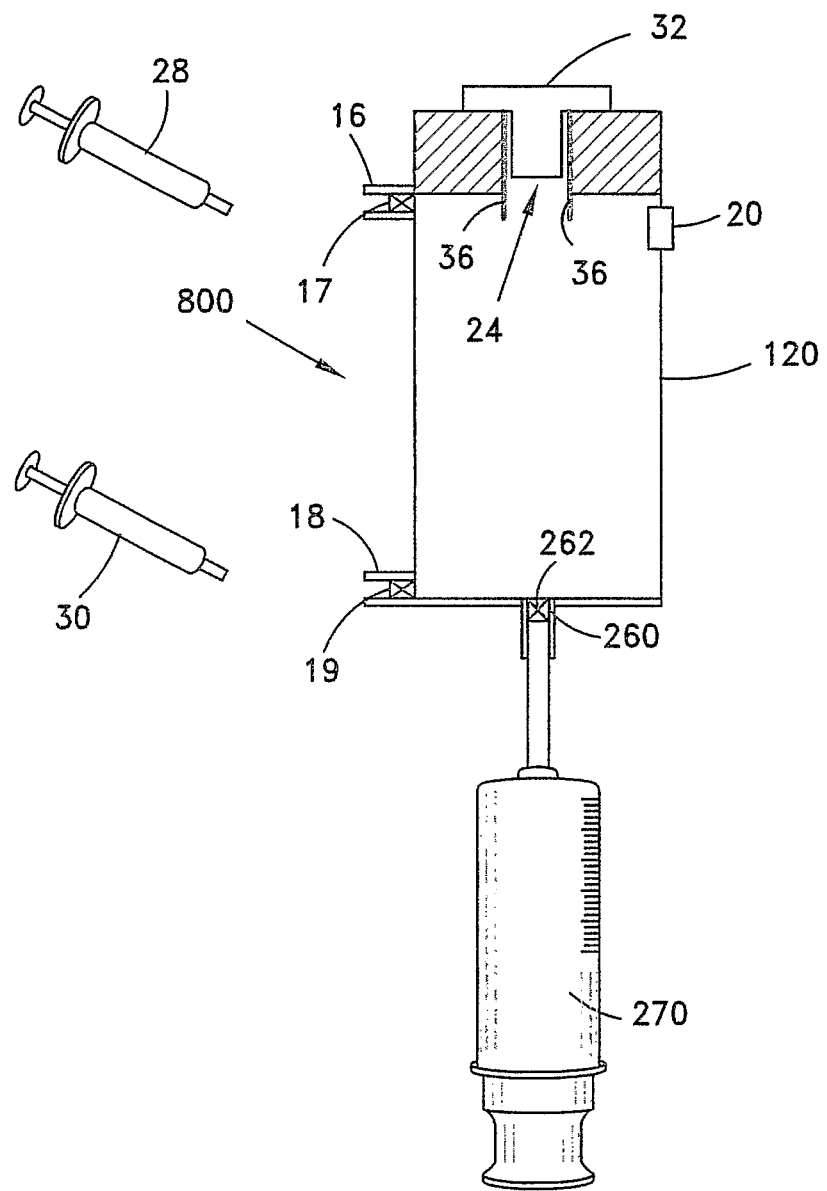
FIG. 1 shows the blood collecting apparatus of the invention.

FIG. 1 is a cross section view showing a first embodiment of the blood collecting apparatus of the invention 800. Apparatus 800 is designed for one time use only, and comes sterilized and is sealed hermetically throughout the process. Apparatus 800 can be made of various types of material, such as glass or plastic. Apparatus 800 comprises disinfection compartment 120, which has a volume of, for example, 50 ml and is connected at the bottom to a blood collection device, for example, but not necessarily, a syringe 270 as shown in the figure. Opening 24, through which the umbilical cord is inserted into apparatus 800, is sealed hermetically by stopper 32, which can be made for example from rubber or plastic. The configuration of this stopper may vary, so long as its function of keeping the apparatus sterile is fulfilled. Since compartment 120 is sealed hermetically throughout the processes of disinfection and blood collection, apparatus 800 includes means, for example a valve and/or an air filter and/or connection to a clean air supply 20, for controlling the pressure inside compartment 120 even as the quantity of liquid in compartment 120 changes. Further details of apparatus 800 will be described herein below.

In order to ensure that the blood vessels of the umbilical cord are clear, the severed tail of the umbilical cord may be shortened by, for example, 1 cm by cutting with a sharp knife. The cord is then squeezed lightly to expel a small quantity of blood and blood clots at its end and disinfected by wiping and/or washing with disinfectant. Before the insertion of the umbilical cord into apparatus 800, holder device 50, shown in FIG. 2a is closed around the loose tail of the umbilical cord. The purposes of holder device 50 are to prevent the leakage of contaminants into apparatus 800, to hold the umbilical cord in place, and to act as a means for grasping apparatus 800.

Figure 2B:
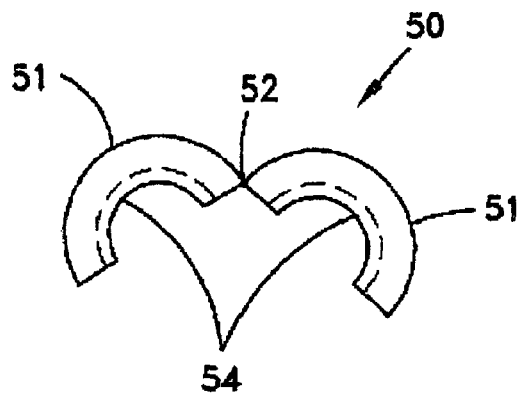
FIGS. 2a to 2c show a holder device for the umbilical cord connected to top of the apparatus of the invention.
Figure 2A:
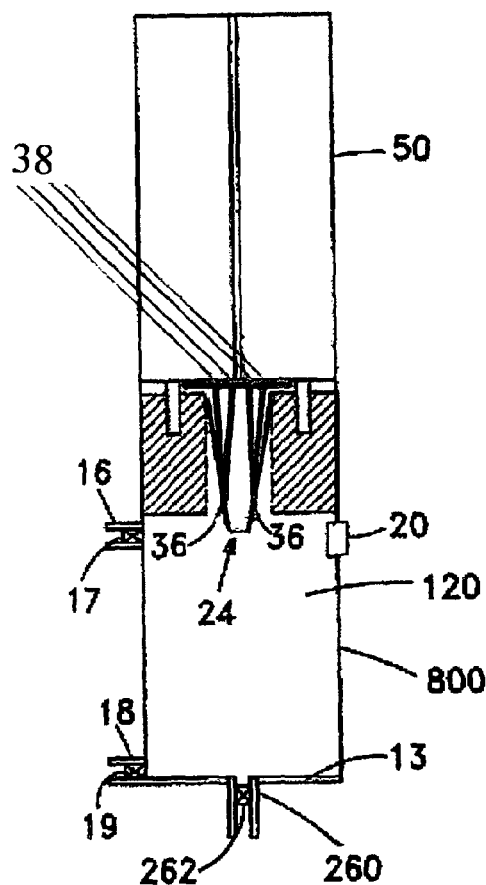
Figure 2C:
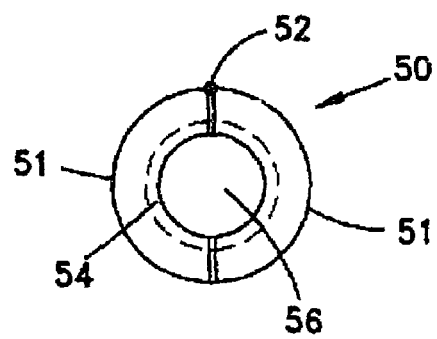

FIG. 2b is a cross section view of holder device 50 in its opened configuration. Holder device 50 can be made from any suitable material, for example, from plastic. As shown in FIG. 2b, holder device 50 consists of two halves 51 connected to one another by connection 52, for example a thin flexible rubber connection or a metal or plastic hinge. Connection 52 allows holder device 50 to be opened and closed. The interior of each half 51 of holder device 50 is covered with a flexible absorbent material 54, for example sponge or absorbent paper or pad. Absorbent material 54 absorbs any contaminants, such as maternal blood, preventing them from flowing down the umbilical cord into apparatus 800. FIG. 2c is a cross section view of holder device 50 in closed configuration. Passage way 56 has a diameter of approximately 10 mm, allowing the umbilical cord to pass through passage way 56 while being held lightly, in order to allow the free flow of blood through the umbilical cord.

Once the umbilical cord is secured in holder device 50, stopper 32 is removed from opening 24. Holder device 50 is then connected to the top of apparatus 800 by conventional means, thereby inserting the cord through opening 24. Returning now to FIG. 1, a sleeve 36, which is attached at its top to the top of opening 24, is shown inside opening 24. Sleeve 36 is initially held tightly against the sides of opening 24 by clasps (not shown in the figure). Connection of holder device 50 to apparatus 800 releases the clasps which hold sleeve 36 in place. Associated with sleeve 36 is a mechanism, such as radial springs 38 which gently pushes the sides of sleeve 36 against the umbilical cord. Sleeve 36 is made of a thin flexible material, e.g. various kinds of latex, silicone or rubber and creates an airtight seal around the cord while exerting a pressure on the walls of the cord that is low enough to allow the blood to flow freely from the cut end of umbilical cord into compartment 120. Since different umbilical cords have different diameters and the diameter of the same cord changes due to changes in the blood pressure inside it, sleeve 36 has the ability to adopt itself to the size and shape of the cord during the blood collection process. When sleeve 36 is sealed around the umbilical cord, opening 24 has a tapered shape which, in the preferred embodiment, narrows down from a diameter of approximately 25 mm at the top to about 5-10 mm at the bottom.

Since disinfection compartment 120 has been opened to the air during the insertion of the umbilical cord through opening 24, there is a need to disinfect this compartment, along with the loose end of the cord inserted into it.

In order to perform this disinfection, compartment 120 may comprises two hubs, shown in FIG. 1, with, for example, luer lock type connections, 16 and 18. In one embodiment of this invention, the hubs are made of the same type of plastic as apparatus 800. In this embodiment hub 16 is located close to the top of compartment 120 and communicates with the interior via a one-way valve 17. Valve 17 allows flow only to the inside of compartment 120. Hub 18 is connected at the bottom side of compartment 120, also via a one way valve 19. Valve 19 allows only outward flow from compartment 12. During the disinfection process two syringes 28 and 30 are used in hubs 16 and 18 respectively. In one embodiment of the invention syringes 28 and 30 have luer lock type connections, so as to fit snugly into hubs 16 and 18 respectively. Valves 17 and 19 enable apparatus 800 to remain hermitically sealed whether a suitable syringe is, or is not, connected to the hub at any given time.

In another embodiment of this invention syringes 28 and 30 have needles at their ends. Hubs 16 and 18 comprise a rubber or plastic stopper, which replace valves 17 and 19 and enable compartment 120 to remain hermitically sealed whether a needle is inserted through the stopper into compartment 120 or is withdrawn.

The disinfection process is carried out as follows: The re-openable cord clamp on the umbilical cord is opened to allow approximately 1 ml of blood to drain into disinfection compartment 120, and is then closed. Syringe 28, which can be either a glass or plastic syringe, is then used in order to inject disinfectant, for example Chlorexidine Alcohol, into compartment 120 through hub 16. The amount of disinfectant injected into compartment 120 should be sufficient to fill the compartment. After approximately 30 seconds syringe 30 is connected through hub 18 to the interior of compartment 120 and used to completely draw the blood and disinfectant out of compartment 120. This disinfection procedure may be repeated one or more times to ensure sterility of the interior of compartment 120.

In one embodiment of this invention a hub 260, for example with a luer lock type connection, is connected to disinfection compartment 120 through a one-way valve 262, which allows flow only out of compartment 120. A blood collection vessel, for example a syringe 270 (as shown in the figure) or a blood collection bag (not shown in drawing), both containing dry or liquid anticoagulant (not shown in the figure), is connected to hub 260. When the process of blood collection is about to begin apparatus 800 is placed in a lower position than the placenta. After the disinfection is performed, as described hereinabove, the re-openable cord clamp is removed from the umbilical cord, valve 262 is opened, and the blood drains with the aid of gravity through compartment 120 into the blood collection vessel.

In another embodiment of this invention a standard 3-way stopcock (not shown in the figure) replaces valve 262. This stopcock may have connections to a blood collection bag and a syringe, used together for collecting the blood.

In another embodiment of this invention a multi sample vacuum tube holder (not shown in the figure) is attached to hub 260. This holder can be used for collecting the blood or for example to remove small blood samples of the collected blood using, for example, standard blood collection vacuum tubes.

Figure 3:
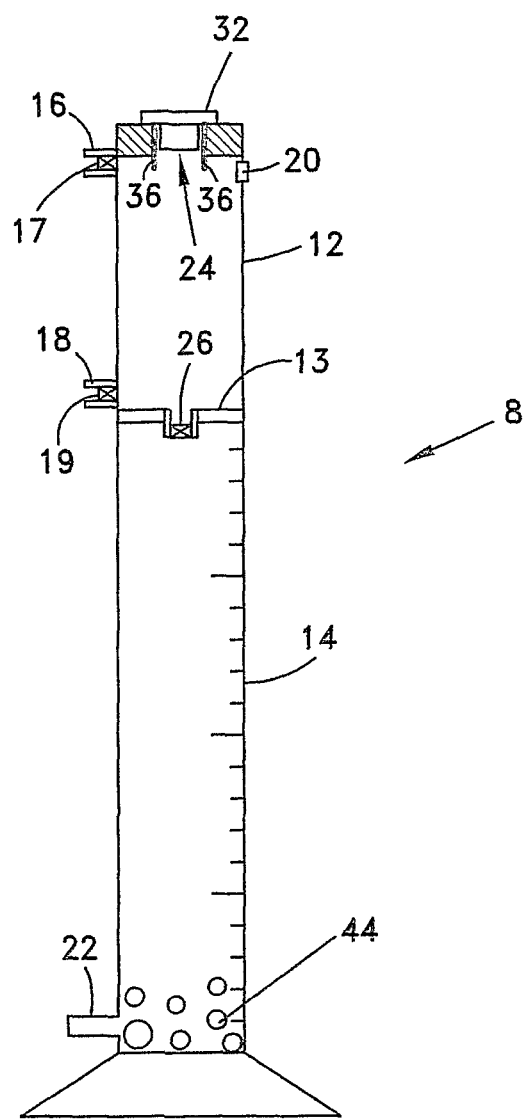
FIG. 3 shows another embodiment of the blood collecting apparatus of the invention.

FIG. 3 is a cross section view of yet another embodiment of the invention. In this embodiment apparatus 8 comprises two compartments; disinfection compartment 12, and collection compartment 14 separated from each other by a partition 13. The two compartments can be isolated from each other, or placed in fluid communication with each other by means of valve 26 in partition 13. Manually operated one-way valve 26 which is made in the preferred embodiment from plastic or metal provides a passageway through partition 13. Valve 26 remains closed, for sterility reasons, until the time when the collection of cord blood begins. Collection compartment 14 has a volume of approximately 300 ml, in this compartment there may be placed anticoagulant 44, for example Heparin or CPD.

In FIG. 3 it is also shown that collection compartment 14 comprises a hub 22, preferably with a luer lock type connection located at its. Hub 22 may be used to connect compartment 14 of apparatus 8 to external objects.

In one embodiment, the blood collection compartment 14 of apparatus 8 is not connected to any external objects. When the process of blood collection is about to begin apparatus 8 is placed in a lower position than the placenta. After the disinfection process, as described hereinabove, valve 26 is opened and the re-openable cord clamp is removed from the umbilical cord. While the blood drains into apparatus 8, the apparatus is shaken, thereby mixing the collected blood with anticoagulant 44. Once the blood has been collected, valve 26 is closed, thereby isolating collection compartment 14 from disinfection compartment 12. The cord is removed from apparatus 8, and the collected blood is stored within collection compartment 14, and taken for further processing.

In another embodiment of the invention, hub 22 is connected to a standard 3-way stopcock (not shown in the figure). This stopcock may have connections to a blood collection bag and a syringe used together for collecting the blood.

Figure 5A:
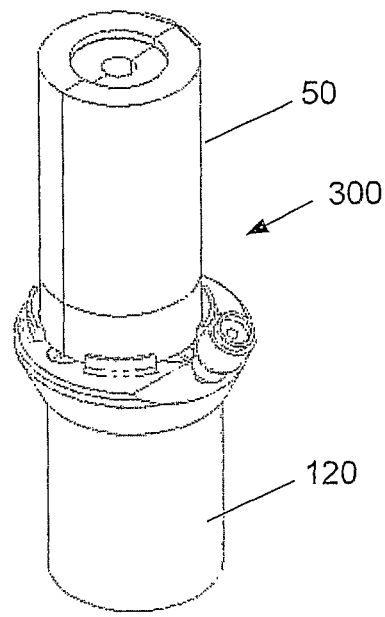
FIGS. 5A to 5E show a preferred embodiment of the blood collection device of the invention.
Figure 5B:
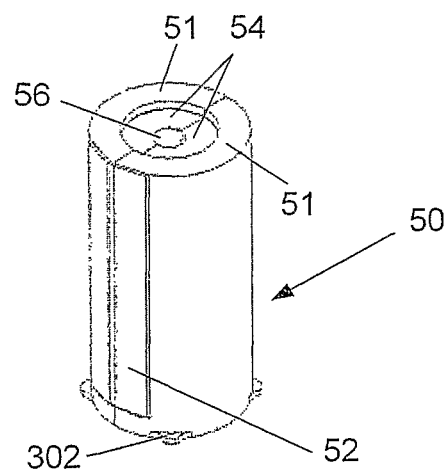

A preferred embodiment of the invention is shown in FIGS. 5A to 5E. In this embodiment, collection apparatus 300 is comprised of two parts: holder device 50 and disinfection compartment 120. As in the embodiment described hereinabove, holder device 50 (see FIG. 5B) is cylindrically shaped and comprised of two halves 51 connected by a hinge 52 that allows the halves to be swung open and closed. The inside of each half 51 is lined with absorbent material 54. When holder device 50 is in its closed configuration, as shown in FIG. 5B, a clear passageway into which the umbilical cord is inserted exists along its longitudinal axis. At the bottom of holder device 50 are several projecting pieces 302, which are used to attach holder device 50 to disinfection compartment 120. At the bottom of each half 51 on the inside is located a half disk of flexible material that forms a collar 316 preventing any fluid from sliding down the outer surface of the cord (see FIG. 5D). Collar 316 can be made of any flexible material, e.g. rubber, which can form a tight seal about the cord, preventing the passage of any fluid down the outer surface of the cord while not restricting the flow of blood through the cord.

Figure 5C:
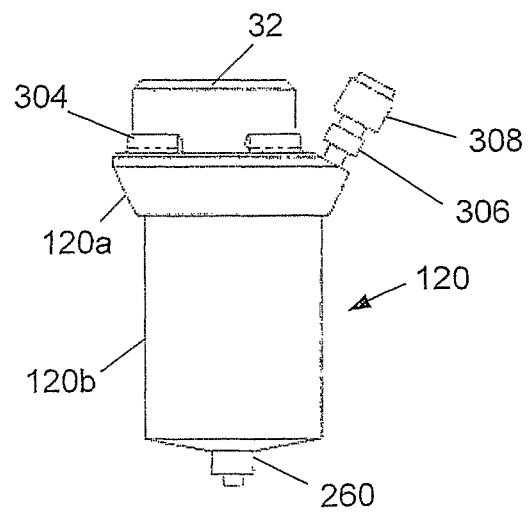

FIG. 5C shows the disinfection compartment 120. In the exemplary embodiment shown in the figures, the disinfection compartment 120 is made of two cylindrically shaped portions, upper portion 120a and 120b, permanently fastened together, for example with the aid of screws 318 (FIG. 5E) to form a container that can be hermetically sealed. Before use the interior of disinfection compartment is kept sterile by sealing the entrance at the top of upper portion 120a with stopper (cover) 32. On the top outside of upper section 120a are several protrusions 304 comprising slots into which projecting pieces 302 on the holder device 50 can be inserted to hold both parts of collection apparatus 300 together. Inside of upper portion 120a is located a sleeve 36 (FIG. 5E) similar to that described with respect to FIGS. 1 and 2a. On the outside of the upper section is a nipple that connects the inside of lower section 120b to the outside environment. The nipple is fitted with a filter 306 and capped with a valve 308 to allow the pressure inside and outside of the apparatus 300 to be equalized by transfer of filtered air. At the bottom of lower portion 120b of disinfection compartment 120 is located a luer connection 260 to allow fluids to be introduced into or withdrawn from lower section 120b.

Figure 5D:
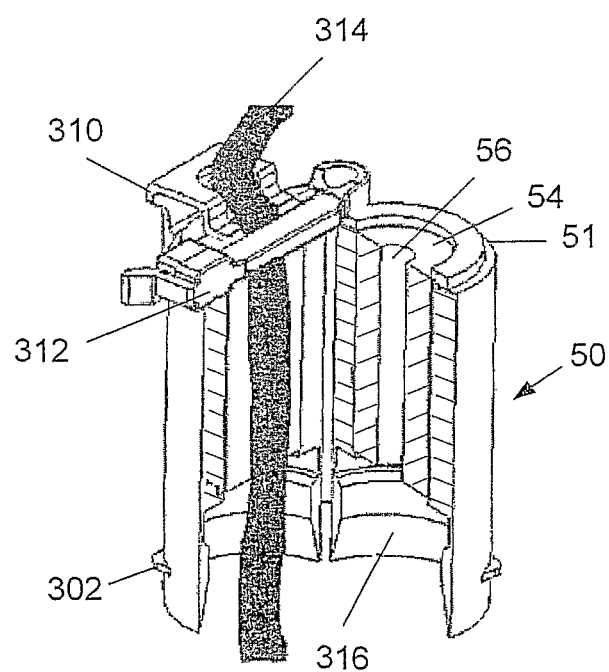
Figure 5E:
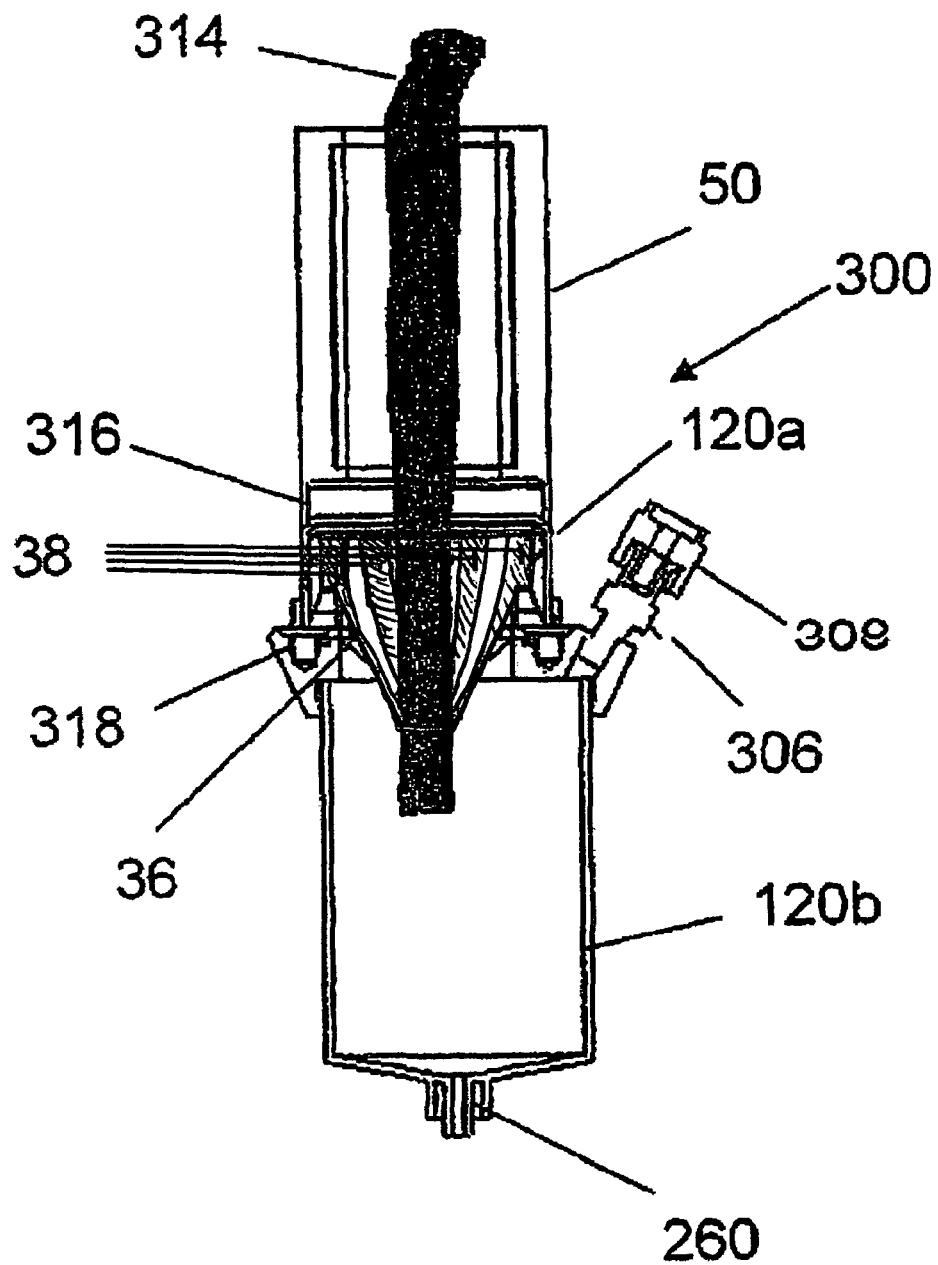

FIGS. 5D and 5E illustrate the major steps in the medical protocol that has been proposed for collecting cord blood using this embodiment of the invention. After birth of the child, the umbilical cord is compressed with a clamp close to the baby and then a second reopenable clamp 312 is attached to the cord about 10 cm above the first clamp. The umbilical cord is now cut between the two clamps close to the clamp on the baby's side and the free end of the cord beneath clamp 312 is disinfected, for example by wiping it with a soft cloth soaked with a disinfectant solution. Now referring to FIG. 5D, which shows holder device 50 in its open configuration, the free end of cord 314 is placed in the passage way 56 through holder device 50. To insure proper placement of cord 314, reopenable clamp 312 rests on the top of holder device 50 and is held in place by retaining clip 310 (clip 310 is not shown in any of the other figures in order to simplify them, but is to be understood to be present in thee preferred embodiment of the holder device). The two halves 51 of holder device 50 are now closed and locked in the closed configuration by a suitable mechanism (not shown in the figures). At this stage, the upper part of the free end of the umbilical cord 314 is held firmly in place by the absorbent material 54 and collar 316 and the lower part of the free end dangles beneath holder device 50.

Now stopper 32 is removed from the opening at the top of disinfection compartment 120 and valve 308 is opened. The end of the cord dangling beneath collection apparatus 50 is carefully inserted through sleeve 36 in the upper portion 102a until holder device 50 rests on top of disinfection compartment 120 and the tip (~1 cm) of the cord 314 projects into the lower portion 120b of the disinfection compartment. The holder device 50 is now rotated relative to disinfection compartment 120 until projecting pieces 302 enter the slots in protrusions 304, thereby locking the two components of collection apparatus 300 together.

After connecting the holder device 50 to the disinfection compartment 120, clamp 312 is opened briefly to allow a few drops of blood to flow into lower part 120b of the disinfection compartment and then the clamp is closed. Disinfectant solution is now injected into lower part 120b by means of a syringe connected to luer connection 260 until lower part 120b is completely full. The disinfectant is allowed to remain inside the disinfection apparatus for a short while, e.g. 30 seconds, and then is drained out by use of the same syringe that was used to fill the apparatus. The syringe with the disinfectant is now disconnected from luer connector 260 and a new one that will be used to collect the cord blood is connected in its place. The valve 308 is now closed, collection device is lowered and supported beneath the placenta, and the clamp 312 is opened. The blood flows into the clean interior of lower portion 120b and is continually drawn into the syringe, aided by the slight negative pressure created by pulling back slowly on the piston of the syringe. If necessary, the collection syringe can be replaced with a new one when it is full, without interrupting the collection process or endangering the sterility of the collected blood. During the collection process it is usually necessary to lightly shake the syringe to mix the anticoagulant agent inside it with the blood.

Ideally, the above procedure is carried out before the birth of the placenta. However if the placenta is born during the collection process, or even before collection of the cord blood begins, the procedure is carried out as described above with provision being made to support the placenta above the collection apparatus. Experienced persons will recognize that the apparatus of the invention allows for a very rapid method of collecting the cord blood. An extremely short learning curve is needed, even for personnel having only a minimum of medical training, in order to achieve optimal results using the method of the invention.

In conventional closed methods, the umbilical cord is clamped in two places and severed between the clamps after the birth of the baby and a standard 16 G needle is inserted into the vein just above the clamp on the free end of the cord. The blood is then drained through a tube into a conventional blood collection bag. A frequent occurrence during the collection procedure is that the rate of blood flow drops severely or even stops because of coagulation of the blood in the vein. In order to overcome this, the needle is withdrawn from the vein and reintroduced into the vein at a location on the cord closer to the placenta. It is very common to have to withdraw and reinsert the needle two or more times in order to try to maximize the amount of cord blood collected. The cord is wiped with disinfectant before inserting the needle and the needle can also be rinsed with a disinfectant before reintroducing it. Some not commonly used procedures require disconnecting the original needle from the tubing and reattaching a new sterile one in its place. However, each time the needle is removed from and reinserted into the vein or detached from a reattached to the tubing, there is a relatively high probability of contaminants entering the tubing and from there into collection bag.

Figure 6:
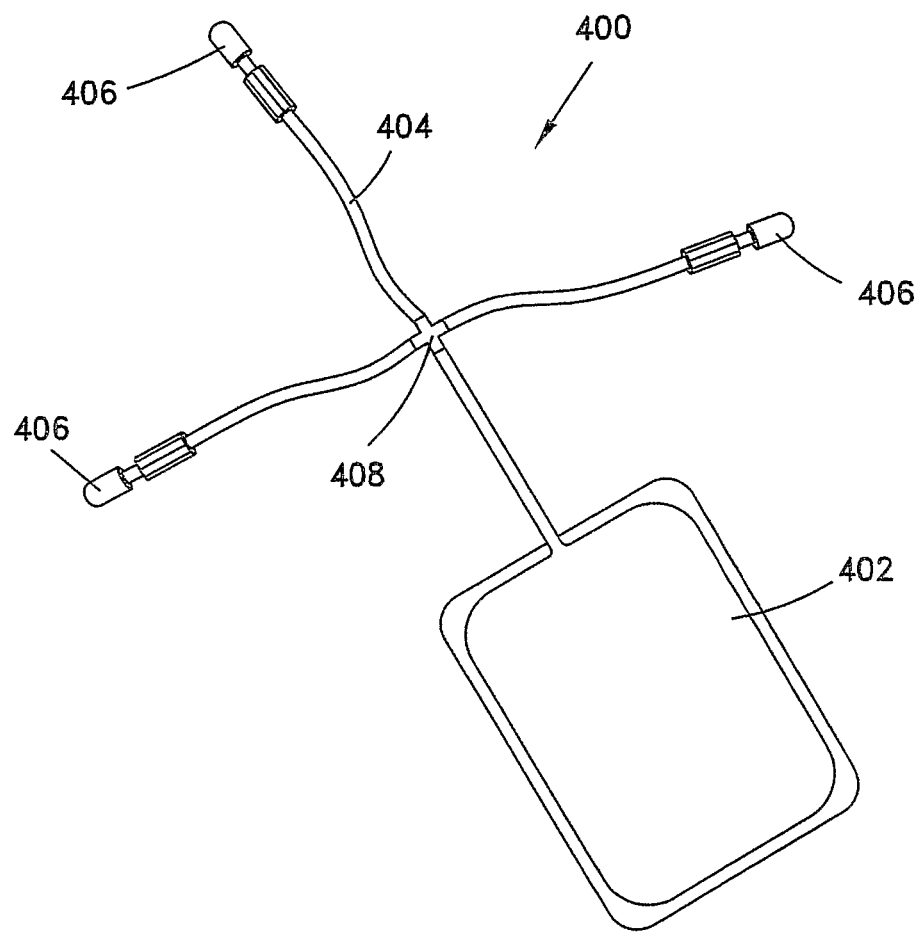
FIG. 6 shows a closed circuit system for collecting cord blood.

In FIG. 6 is shown a closed collection system 400 that allows an improvement in the amount and sterility of cord blood collected when compared to the closed system methods currently employed. System 400 comprises a blood collection bag 402 to which is connected at least three needles or IV-cannulas 406—all with sterility covers, by means of tubing 404 and cross 408. Using this system the risk of contamination is greatly reduced. As in the prior art, the first needle is inserted into the vein near the bottom of the cord. When the rate of flow of the blood decreases the second needle is inserted and then the third one. The needles need not be withdrawn and therefore the integrity of the closed collection circuit is maintained and no contaminants can enter blood collection bag 402. If it is desired to withdraw one or more of the needles while blood is still be collected using one or more of the other needles, than valves can be provided, either on the proximal end of the needles 406 or on cross 408. Other configurations for system 400 are contemplated by the inventor. For example, the piece of tubing 404 connected to each of the needles 406 can be connected directly to collection bag 402.

The system 400 of the invention has two other features that distinguish it from prior art systems. Firstly, all prior art systems known to the inventor use a 16 G needle, which has an outer diameter of 1.7 mm. Recognizing that the diameter of the vein in the umbilical cord is typically 4 mm when full with blood and 2 mm when empty, larger diameter syringes or IV-cannulas needles 406, for example either 10 G or 12 G, which have outer diameters of 3.2 mm and 2.6 mm respectively, can advantageously be used. By using the larger needles the blood will be collected faster allowing more blood to be collected before significant coagulation of the blood in the vein occurs. The second feature of system 400 is that, because of the greater amount of cord blood collected, collection bag 402 is much larger than collection bags used in the prior art. Bag 400 is at large enough to collect at least 200 ml of cord blood in addition to any anticoagulant solution or powder that is present.

System 400 of the invention can be used in another closed-circuit method of collecting blood. In this method a connection is made to all three blood vessels of the umbilical cord in order to be able to collect blood from the highest number of vessels possible. In the prior art, for example, as stated in U.S. Pat. No. 6,302,854, it is commonly thought that due to the limited cross-section of the two arteries of the umbilical cord, the collection of blood using a close-circuit system is only feasible through the vein of the umbilical cord. In comparison to the prior art, the amount of collected blood can be significantly increased by collecting blood from all three vessels of the umbilical cord.

Figure 4:
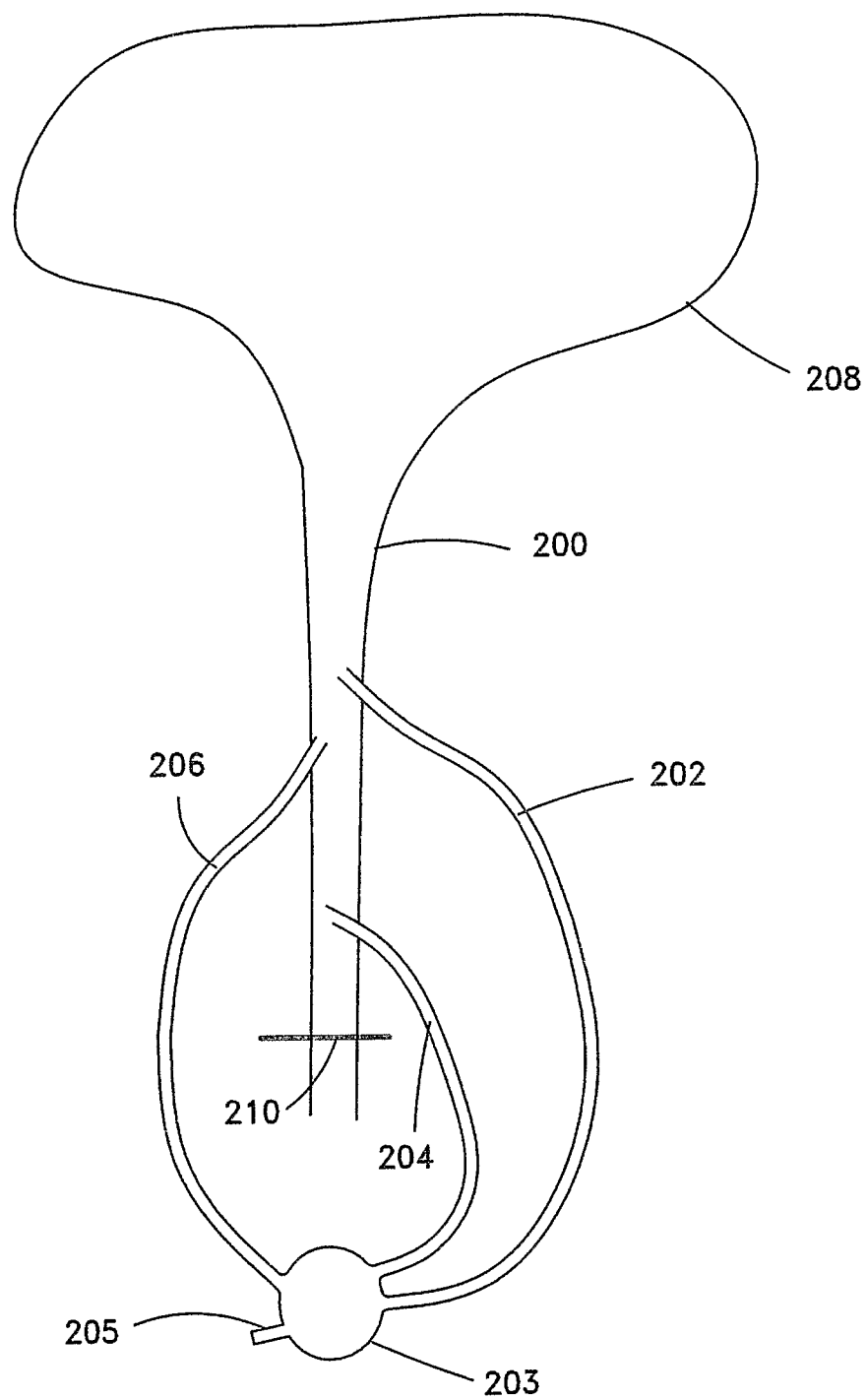
FIG. 4 schematically shows the umbilical cord attached to the placenta and to three IV-cannulas or needles.

FIG. 4 shows an overview of the umbilical cord 200, connected at one end to three IV-cannulas (Intravenous & arterial) or needles 202, 204 and 206 and at the other end to the placenta 208. The umbilical cord 200 is squeezed with a cord clamp 210, made for example from plastic or metal. In order to begin the blood collection procedure, cannulas 202, 204 and 206, comprising needles (not shown in the figure), are inserted into each of the three vessels of the umbilical cord aided by said needles. After inserting the cannulas, the needles are removed leaving the distal end of a cannula inside the two arteries and vein of the umbilical cord. IV-cannulas 202, 204 and 206 are then secured to the umbilical cord, using tape for example, in order to keep them from disconnecting from the cord. The cannulas are then connected to a blood collecting means by means of valves and connectors (not shown in the figure) located on their distal end.

In one embodiment of the invention, the blood is collected simultaneously from all three blood vessels through connector 203, which comprises a port 205, which can be made for example from plastic. Port 205 connects to the three IV-cannulas or needles at its input side and on its output side to a blood collection vessel (not shown in the figure), for example a syringe, a blood collection bag, or both via a 3-way stopcock. The valves on cannulas 202, 204 and 206 are opened, thus allowing the blood to flow from the umbilical cord through the cannula into the said blood collection vessel/s.

In another embodiment of the invention a blood collection vessel (not shown in the figure), for example a syringe or a blood collection bag, is connected to the loose end of each of the three cannulas 202, 204 and 206. The blood collection process is as described hereinabove, with the exception that the blood is collected independently from each of the three blood vessels into three separate blood collection vessels.

In yet another embodiment of the invention, between cannulas 202, 204, and 206 and the blood collecting vessel (or vessels) one or more multi sample vacuum tube holders (not shown in the figure) are connected be means of standard "T" or "Y" connectors. These holders can be used for collecting the blood or for removing small blood samples of the collected blood using, for example, standard blood collection vacuum tubes.

Although embodiments of the invention have been described by way of illustration, it will be understood that the invention may be carried out with many variations, modifications, and adaptations, without exceeding the scope of the claims.

The invention claimed is:

1. An open circuit collecting apparatus (OCA) comprising,
    a) a cord carrying holder for enclosing and holding an upper unsevered external extremity of an umbilical cord, said holder is formed of two halves connected one to the other, said halves forming a closed passage way upon closing one to the other, through which said umbilical cord is inserted; and,
    b) a disinfection compartment in which said held cord is disinfected, said compartment comprising an air filter located at an upper portion of said compartment and adapted to provide controllable sterile air-flow communication with an interior environment of said compartment, a tapered opening located at a top base of said compartment, a flexible sleeve adapted to be inserted through said opening, said sleeve adapted to be inserted through said opening and provide an airtight seal around said cord whilst exerting low enough pressure on walls of said cord as to allow blood to flow freely from a cut end of said cord, at least one hermetically sealable hub opening for injecting and drawing disinfectant from said disinfection compartment, said hub opening further provided with a valve for said sealable hub opening;
    wherein said holder is attached to said disinfection compartment and adapted to hold said cord over said disinfection compartment, such that free flow of high volumes of cord blood from a severed umbilical cord is facilitated, said flow occurring in an essentially sterile manner.

2. An OCA according to claim 1 wherein said holder further comprising projecting pieces adapted to reversibly attach to protrusions located at the upper portion of said disinfection compartment further wherein said holder is adapted to insert said end of said cord into said interior of said disinfection compartment.

3. An OCA according to claim 1 further wherein said tapered opening is adapted for insertion of said cord carrying holder, said opening activated to open and close by said cord carrying holder, such that a cord tip projects into a lower portion of said disinfection compartment and is held by said sleeve and said opening in an airtight manner such that free flow of high volumes of cord blood from a severed umbilical cord is facilitated, said flow occurring in an essentially sterile manner.

4. An OCA according to claim 1 wherein an interior of said holder is covered with flexible absorbent material for absorption of contaminants and lightly grasping of said cord in a manner such that free flow of high volumes of cord blood from a severed umbilical cord is facilitated.

5. An OCA according to claim 1 wherein said sleeve further comprising means for holding against said cord, said means comprising radial springs.

6. An OCA according to claim 1 wherein said holder device comprises at least two hinged parts for enclosing said two halves of said holder around said cord.

7. An OCA according to claim 1 wherein said OCA additionally comprises at least one blood collection vessel connected to and in hermetic fluid connection with said interior of said disinfection compartment.

8. An OCA according to claim 1 wherein said holder is disposable.

9. An OCA according to claim 1 wherein said disinfecting chamber is disposable.

10. An OCA according to claim 7 wherein said blood collection vessel is disposable.

11. An OCA according to claim 1 further comprising a reopenable clamp integrated at top base of said holder, said clamp is adapted to hold said umbilical cord and control blood flow through said cord.

* * * * *